United States Patent [19]

Pound et al.

[11] Patent Number: 5,230,727
[45] Date of Patent: Jul. 27, 1993

[54] AIR FILTER FOR MEDICAL VENTILATION EQUIPMENT AND THE LIKE

[75] Inventors: Robert D. Pound, Erie; Lockett E. Wood, Louisville, both of Colo.

[73] Assignee: Cybermedic, Inc., Boulder, Colo.

[21] Appl. No.: 894,447

[22] Filed: Jun. 5, 1992

[51] Int. Cl.⁵ .............................................. B01D 46/10
[52] U.S. Cl. ...................................... 55/492; 55/494; 55/501; 55/511; 210/446
[58] Field of Search ................ 55/492, 494, 495, 501, 55/502, 503, 510, 511, 524; 210/445, 446, 447, 455

[56] References Cited

U.S. PATENT DOCUMENTS

| | | |
|---|---|---|
| 3,684,100 | 8/1972 | Close . |
| 3,782,083 | 1/1974 | Rosenberg . |
| 3,815,754 | 6/1974 | Rosenberg . |
| 3,932,153 | 1/1976 | Byrns ................................. 55/511 |
| 4,113,627 | 9/1978 | Leason ............................. 210/446 |
| 4,187,182 | 2/1980 | Rosenberg . |
| 4,360,018 | 11/1982 | Choksi . |
| 4,386,948 | 6/1983 | Choksi et al. . |
| 4,444,661 | 4/1984 | Jackson et al. ...................... 210/446 |
| 4,657,570 | 4/1987 | Gronholz et al. ................ 55/501 X |
| 4,798,676 | 1/1989 | Matkovich . |
| 4,818,258 | 4/1989 | Vann, III . |
| 4,874,513 | 10/1989 | Chakraborty et al. . |
| 4,900,302 | 2/1990 | Newton . |
| 4,917,942 | 4/1990 | Winters . |
| 4,950,317 | 8/1990 | Dottermans . |
| 4,995,310 | 2/1991 | van der Lijn et al. . |
| 5,011,555 | 4/1991 | Sager ................................. 55/511 X |
| 5,047,010 | 9/1991 | Ames et al. . |
| 5,049,170 | 9/1991 | Parnoff . |

Primary Examiner—Charles Hart

[57] ABSTRACT

An inexpensive, bi-directional, low flow resistance air filter for medical ventilation equipment and the like includes a disposable shell possessing a cylindrical conduit terminating in an exponentially curved radially outwardly flaring surface. The exponentially curved construction minimizes dead space and hence also flow resistance Radially and axially spaced stepped annular surfaces connected by short axially extending cylindrical sidewall portions at a distal end of the shell function as coupling and sealing surfaces. A ring of adhesive applied adjacent a peripheral edge of an electret filter disk mounts the filter disk internally within the shell. An elastic retaining band detachably secures an equipment connection adapter to the shell, such that a technician may easily and quickly replace the shell and filter. The equipment connection adapter possesses clamping ring and coupling rim surfaces dimensioned in close conformance with the coupling and sealing surfaces of the shell to ensure a fluid tight connection. The filter assembly allows rapid replacement of contaminated filter components to protect patients from diseases caused by bacterial and viral microorganisms, while minimizing medical waste.

26 Claims, 5 Drawing Sheets

AIR FILTER FOR MEDICAL VENTILATION EQUIPMENT AND THE LIKE

BACKGROUND OF THE INVENTION

Field Of The Invention

Pulmonary function testing equipment, such as spirometers, lung analyzers, etc., assess lung capacity by measuring and/or analyzing the flow, volume, and specific composition of expired gases. These tests and certain associated parameters have been standardized by The American Thoracic Society (ATS). ATS has developed a list of mechanical factors for each test which must be met in order to ensure continuity of testing and test results Ventilation equipment, such as respirators and ventilators, also depends on specific air flows and volumes to operate effectively.

Both testing equipment and treatment equipment require simultaneous fluid connection to the equipment and the patient's mouth, or the vicinity of the mouth. An exhaled breath is composed of dry and humidified gases which provide a medium for bacterial and viral transfer that could contaminate such equipment. Additionally, the patient may be salivating, or separate rubber or cardboard mouthpieces used in pulmonary function testing can stimulate the production of saliva, which then drips, or flows, into equipment components. Therefore, there is a risk of contamination of equipment components from microorganisms borne in saliva as well as expired gas. In the absence of an effective filter, bacteria and viruses can be deposited on the equipment. If testing or treatment equipment were to become contaminated, subsequent patients would be at risk of contacting many diseases, including, but not limited to tuberculosis, pneumocystis carinii pneumonia, HIV, hepatitis, herpes, and the common cold.

The inconvenience and expense of sterilizing equipment components between patients severely limits, in practice, the number of medical professionals who actually sterilize such equipment after each patient. Until recently, medical professionals assumed that a disposable cardboard mouthpiece, or clean rubber mouthpiece, was adequate protection from cross-contamination. In the current environment of drug resistent bacterial and viral strains, there is a growing awareness of the need for adequate, low cost protection.

Description Of The Prior Art

A low pressure drop bacterial filter such as that disclosed by Matkovich in U.S. Pat. No. 4,798,676 has been used in some circumstances. The design of that filter requires that the entire polypropylene housing and filter be discarded after one use. With medically contaminated waste becoming an increasing environmental threat, fully disposable filter assemblies, such as those of the type disclosed by Matkovich and others, are no longer desirable due to the increasing burden of medical waste disposal. Additionally, recent tests have shown that the Matkovich filter does not trap all airborne particles when propelled at high airflow pressures consistent with the first seconds of Forced Expired Volume Testing (FEV).

Effective pulmonary function assessment, and effective and safe ventilator functioning, rely on the accommodation of high air flows and low resistance to those flows. The filter disclosed by U.S. Pat. No. 3,556,097, like many other filters in common usage, possesses large tubular configurations which create sizeable amounts of dead space. A pocket of dead space limits the free flow of fluid through the filter. Consequently, the patient could be rebreathing carbon dioxide. In the case of pulmonary function testing, the clinical impact of the dead space would seriously effect the analysis of expired gases. In artificial ventilation, the impact could be life-threatening.

Chakraborty et al. describe in U.S. Pat. No. 4,874,513 a fully disposable filter with filter support structure disposed at both sides of the filter element. The funnel-shaped filter disclosed by Chakraborty et al. is designed to resist pressure. In testing lung capacity, it is important that the filter act as a conduit for gases and not be obstructive or resistant to pressure. The Chakraborty et al. filter substantially disrupts flow due to the provision of numerous concentric rings and filter media supporting webs which meet the rings at right angles. The webbing of support rings creates substantial flow disturbance, therefore making the Chakraborty et al. filter undesirable for pulmonary function testing or ventilation applications.

U.S. Pat. No. 3,782,083 to Rosenberg describes a disposable gas filter, however, the filter is designed so that the components are bonded together permanently such that the entire filter must be disposed. Also the filter construction is believed to result in a relatively large dead air space.

Several patents have been issued for filtration media which screens bacteria and viruses. U.S. Pat. No. 4,917,942 discloses a non-woven filter material and U.S. Pat. No. 4,863,602 discloses a flexible filtering material disposed in layers. Placement of filter media is critical to assure full and secure coverage without compromising air flow. Some filters require the end-user to place the filtration media in the filter housing prior to use. It is difficult to securely and reliably seal the filter media in the housing without any possibility of leakage of fluids or microorganisms past the filter by simply placing material at an assembly point. Quality control would be served best if the filtering material were easily affixed at the point of manufacture, prior to distribution to the end user.

SUMMARY OF THE INVENTION

In order to achieve these and other objects of the invention, the present invention provides an improved inexpensive, bi-directional, low flow resistance air filter for medical ventilation equipment and the like which includes a disposable shell possessing a cylindrical conduit terminating in an exponentially curved radially outwardly flaring surface. The exponentially curved construction minimizes dead space and hence also flow resistance. Radially and axially spaced stepped annular surfaces connected by short axially extending cylindrical sidewall portions at a distal end of the shell function as coupling and sealing surfaces. A ring of adhesive applied adjacent a peripheral edge of an electret filter disk mounts the filter disk internally within the shell. An elastic retaining band detachably secures an equipment connection adapter to the shell, such that a technician may easily and quickly replace the shell and filter. The equipment connection adapter possesses clamping ring and coupling rim surfaces dimensioned in close conformance with the coupling and sealing surfaces of the shell to ensure a fluid tight connection. The filter assembly allows rapid replacement of contaminated filter components to protect patients from diseases caused by bacterial and viral microorganisms, while minimizing medical waste.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced an carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT(S)

Referring now to the drawings, wherein like reference numerals designate corresponding structure throughout the views, and referring in particular to FIGS. 1 through 5, an improved air filter for medical ventilation equipment and the like according to a first preferred embodiment of the invention consists of an assembly of four separate components: a disposable shell 9, a filter disk 20, a retaining band 30, and an equipment connection adapter 39.

The disposable shell 9 includes a cylindrical tubular conduit 11 terminating at a proximal end in a circular inlet aperture 10 adapted for connection to a patient directly or via conventional mouthpieces, masks, hoods, or tubes, for the purpose of directing exhaled gases from the patient through the filter disk 20. In spirometry testing, in particular, conduit 11 may be employed as a patient mouthpiece to obviate the requirement for a separate disposable mouthpiece, thus minimizing medical waste. The conduit 11 flares radially outwardly toward a distal axial end of the shell 9 in a smoothly exponentially curved surface 15 defined by the equation $R = A + BP^{(CD+G)}$ where R is the radius of the surface 15 from the central longitudinal axis of the shell 9; A is the radius of the inlet aperture 10 (i.e., one-half of the distance shown as Y in FIG. 1); B is a selective variable; P is the base of the number system (e.g., 10 or e); C is a selective variable; D is the axial distance from the lower end of a cylindrical conduit portion 11 at the intersection with exponentially curved surface 15; and G is a selective variable. In the preferred embodiment, A equals 1.27 cm.; B equals 0.002466; P equals e; C equals 0.0246986; and G equals 74.096 (recall R is a function of D).

The exponentially curved surface 15 facilitates more uniform air flow distribution through the disk 20, while confining dead space volume within the limits specified by The American Thoracic Society.

The exponentially curved surface 15 terminates in a short, axially extending, cylindrical sidewall portion 12, which terminates at a ninety degree junction with an increased diameter circular annular step 16 lying in a plane perpendicular to the central longitudinal axis of the shell 9. Step 16 terminates at a radially outer peripheral edge in a ninety degree junction with an axially extending, second short cylindrical sidewall portion 13, which in turn terminates at a ninety degree junction with a second increased diameter circular annular step 14 lying in a plane perpendicular to the central longitudinal axis of the shell 9. The disposable shell 9 may be integrally molded utilizing conventional methods from a variety of materials including: polyethylene, polypropylene, vinyl, nylon, rubber, various impregnated or laminated fibrous materials, various plasticized materials, cardboard, paper, etc. A preferred embodiment employs molded polystyrene.

The filter 20 may utilize any conventional filter media, but preferably employs a synthetic polypropylene media comprising permanent electrets in the form of a fibrous mat combined with spunbonded polypropylene cover webs, available under the trademark FILTRETE from Minnesota Mining and Manufacturing Corporation (3M). Electrets consist of a non-conductive fiber possessing embedded electrical charges, resulting in the attraction and entrapment of oppositely charged contaminant particles. This type of filter has only one-tenth the air flow resistance of other filtration media, as disclosed in U.S. Pat. No. 4,917,942, the entire disclosure of which is incorporated by reference herein. As a result, exhaled gases can be expelled at flows as high as 16 liters per second, or 960 liters per minute. In tests, an example embodiment of the filter assembly of the present invention, utilizing a disposable shell 9 (FIG. 1) possessing a maximum diameter X of about 4.5 inches, a minimum diameter Y of about 1.0 inches, and an axial length of about 2.0 inches, achieves a back pressure of only 1 centimeter of water per liter per second at a volumetric flow rate of 12 liters per second, well within the guidelines recommended by The American Thoracic Society (ATS). Further, the inventive filter assembly enables free air flow with a dead space volume of only 50 cubic centimeters from the patient inlet 10 of the disposable shell 9 to the outlet aperture 40 of the adapter 39.

Figure 1:
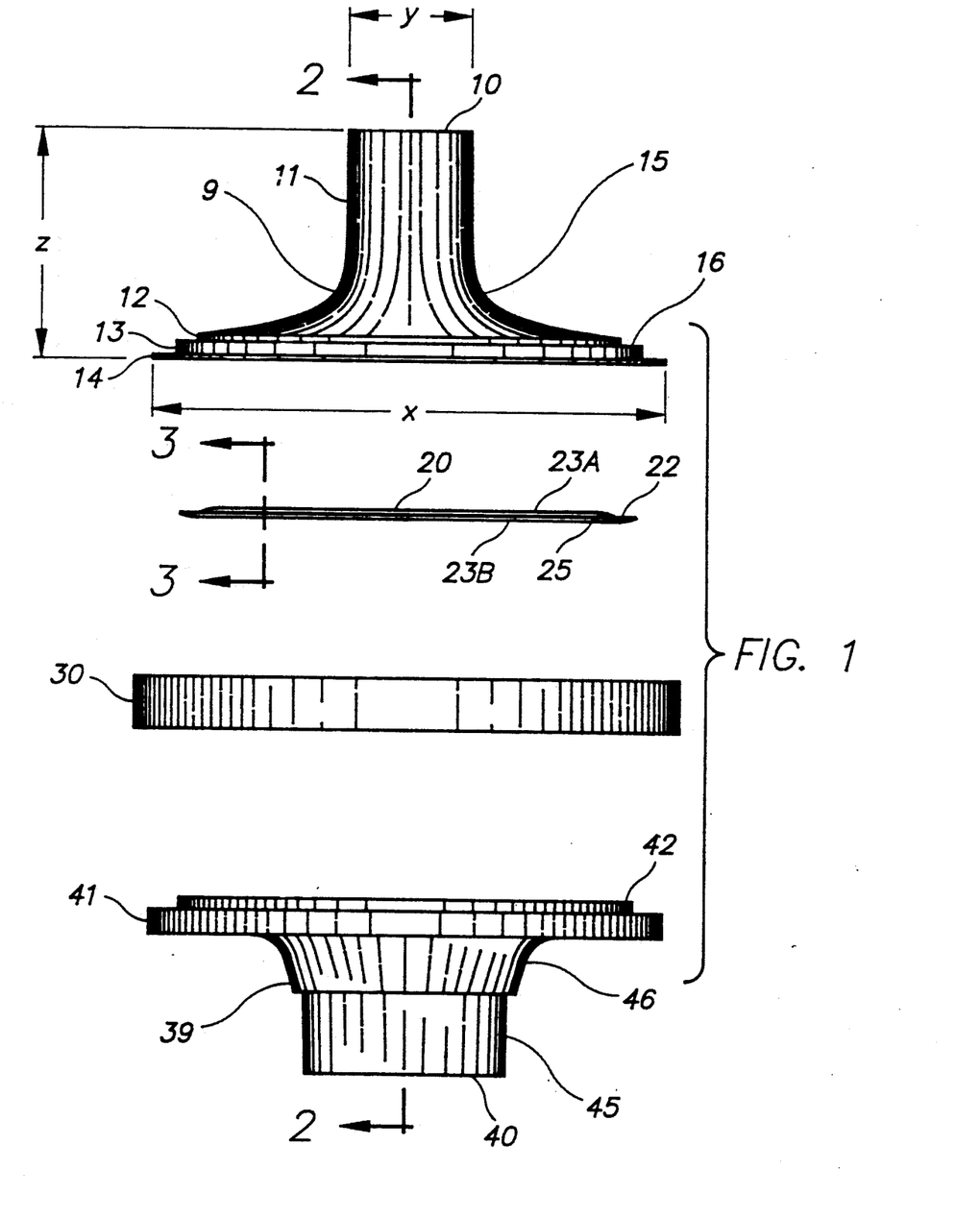
FIG. 1 is an exploded side elevational view of the air filter according to the present invention.
Figure 2:
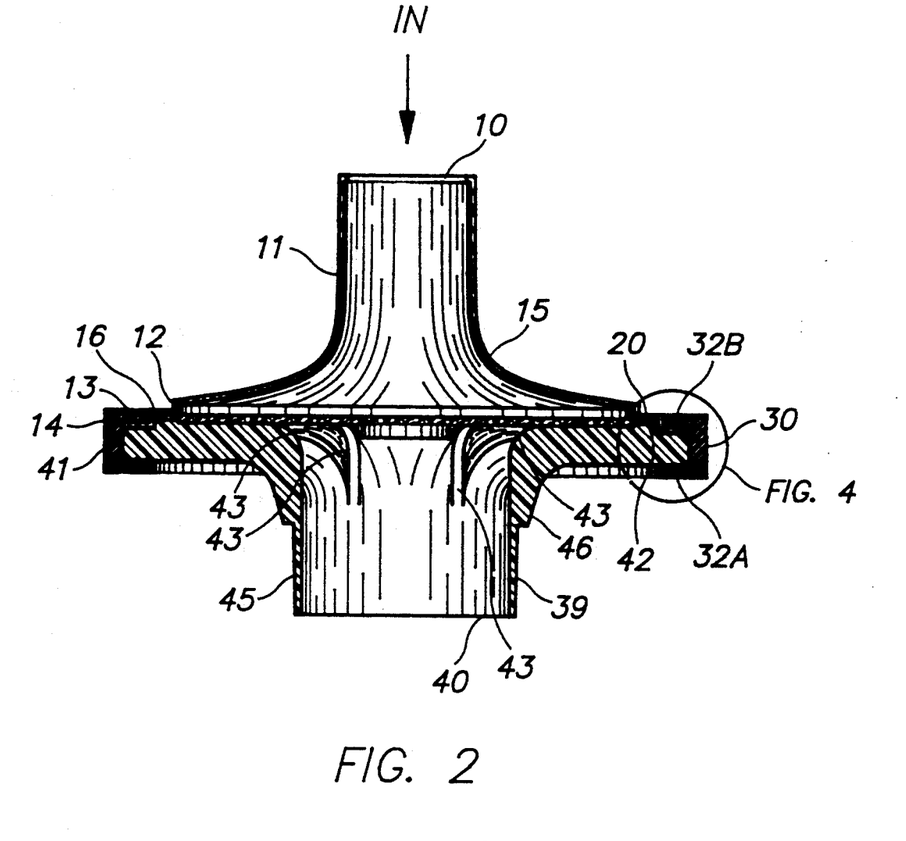
FIG. 2 is an assembled longitudinal cross-sectional view, taken along line 2—2 of FIG. 1.
Figure 3:
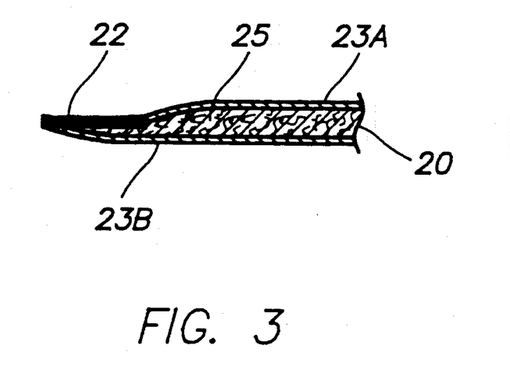
FIG. 3 is an enlarged partial cross-sectional detail view, taken along line 3—3 of FIG. 1, illustrating the details of the filter media construction.
Figure 4:
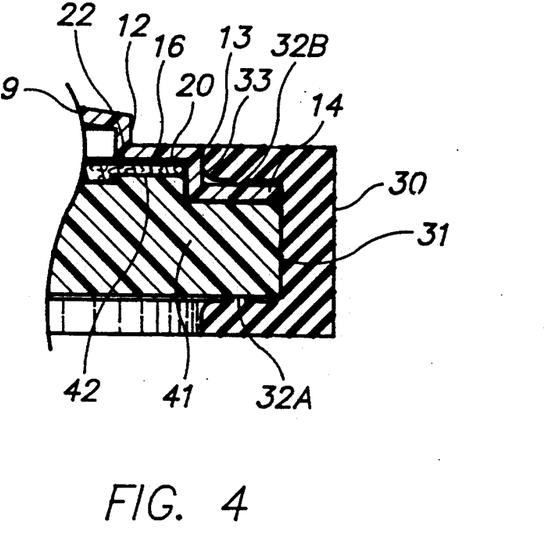
FIG. 4 is an enlarged cross-sectional detail view illustrating the clamping assembly securing the components of the air filter in an assembled condition.

As best shown in FIG. 3, the filter disk 20 preferably includes a central filter media core 25 sandwiched between an inner cover web 23A and an outer cover web 23B. Inner web 23A and outer web 23B function as initial and final filtration screens, respectively. An annular adhesive ring 22 disposed adjacent a peripheral edge of the upper cover web 23A secures the filter disk 20 to an interior face of annular step 16 of the disposable shell 9, as depicted in FIGS. 2 and 4. Cylindrical sidewall portion 12 of shell 9 forms a small, thin cylindrical disk-shaped dead space adjacent to the cover web 23A of the filter disk 20, which, in conjunction with outwardly flaring surface 15, ensures uniform distribution of fluid flow through the surface of disk 20. The axial length of the sidewall portion 12 is preferably approximately one-tenth of an inch. If the distance is substantially greater then the volume of dead air space undesireably increases, but if the distance is substantially shorter then air flow is undesireably restricted in that peripheral region. A very important advantage of this construction is the capability of bi-directional filtration.

An equipment connection adapter 39 includes a tubular cylindrical conduit portion 45 possessing a circular outlet aperture 40 at a distal end adapted for connection to medical ventilating equipment or pulmonary testing equipment or both utilizing conventional 22 mm. tubing or other connections. The equipment connection adapter 39 may be dimensioned in various different sizes and configurations for connection with a variety of different conventional equipment. The adaptor 39 is principally intended as a reusable item, but may be inexpensively formed so as to be readily disposable, within the scope of the invention. The adaptor 39 may be integrally molded from the materials listed above as suitable for use in fabrication of the shell 9.

Figure 5:
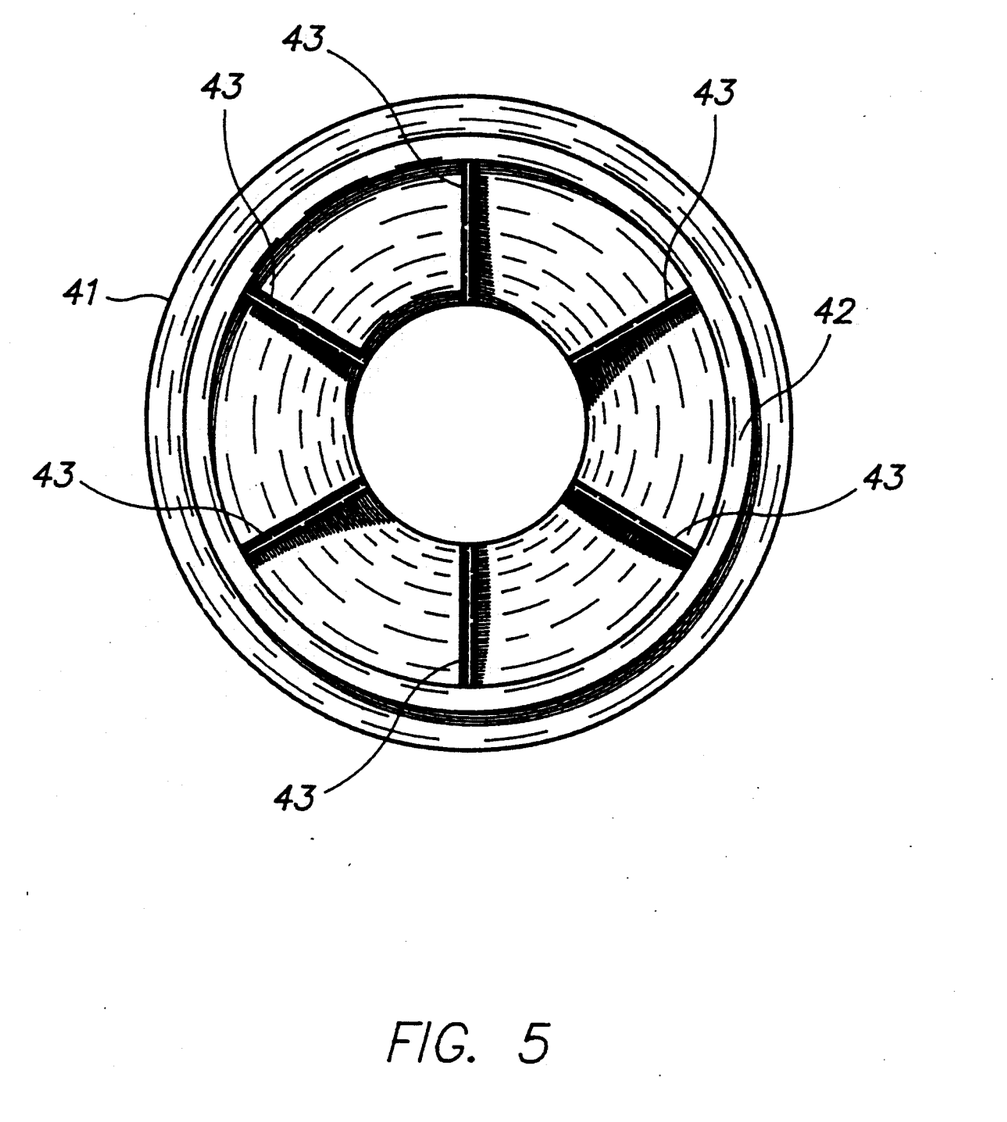
FIG. 5 is a top plan view illustrating the equipment connection adaptor component of the air filter of the present invention.

An axially upwardly and radially outwardly flaring tubular portion 46 connects the conduit portion 45 to a cylindrical coupling rim 41. As shown in FIGS. 2 and 5, a plurality of generally L-shaped ribs 43, spaced at equal sixty degree circumferential increments, extend from an interior sidewall of the conduit portion 45 to an upstanding circular clamping ring 42 disposed on a proximal end face of equipment connection adapter 39. Upper surfaces of the radially extending leg portions of ribs 43 function to support filter disk 20 so as to prevent collapse of the filter disk 20 upon fluid flow in the direction of the arrow labeled "IN" in FIG. 2. As can be appreciated from FIGS. 2 and 4, clamping ring 42 clamps or compresses a circular outer peripheral edge portion of filter disk 20 (coated with an adhesive 22), against an interior surface of annular step 16. The axial extent of cylindrical wall portion 13 of disposable shell 9 closely conforms to the combined thickness of filter disk 20 and clamping ring 42, such that annular step 14 abuts a proximal circular annular surface of coupling ring 41. These abutting surfaces form multiple sealing junctions, ensuring an air-tight seal between the shell 9 and adaptor 39.

An elastic retaining band 30, preferably formed from a rubberized latex material, functions to releasably secure disposable shell 9 and adhesively attached filter disk 20 to the equipment connection adapter 39, such that a technician may easily and quickly replace the shell 9 and disk 20 without detaching adapter 39 from associated ventilation equipment. With reference to FIG. 4, the generally cylindrical retaining band 30 includes an internal circumferential groove 31 dimensioned such that an internal cylindrical sidewall 33 of band 30 abuts cylindrical sidewall portion 13 of shell 9, while the cylindrical axially extending sidewall of groove 31 abuts outer axially extending cylindrical sidewall surfaces of coupling rim 41 and annular step 14. Coaxial juxtaposed circular sealing beads 32A and 32B, integrally formed on parallel lower and upper circular annular interior surfaces of band 30 function to reinforce the union of shell 9 with adaptor 39 and also provide an auxiliary seal to prevent fluid escape or entrainment.

Figure 6:
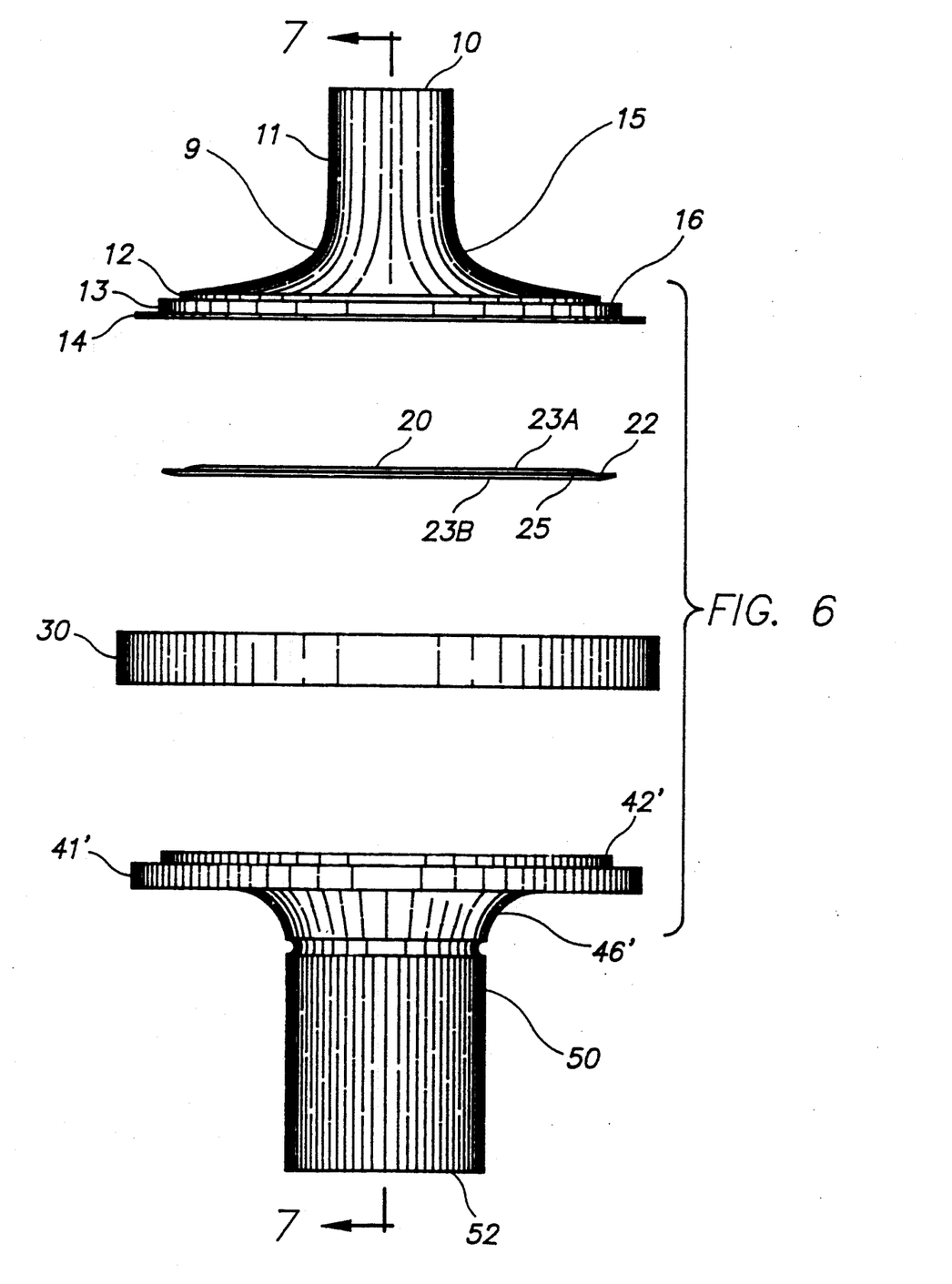
FIG. 6 is an exploded side elevational view of the air filter according to another embodiment of the present invention.
Figure 7:
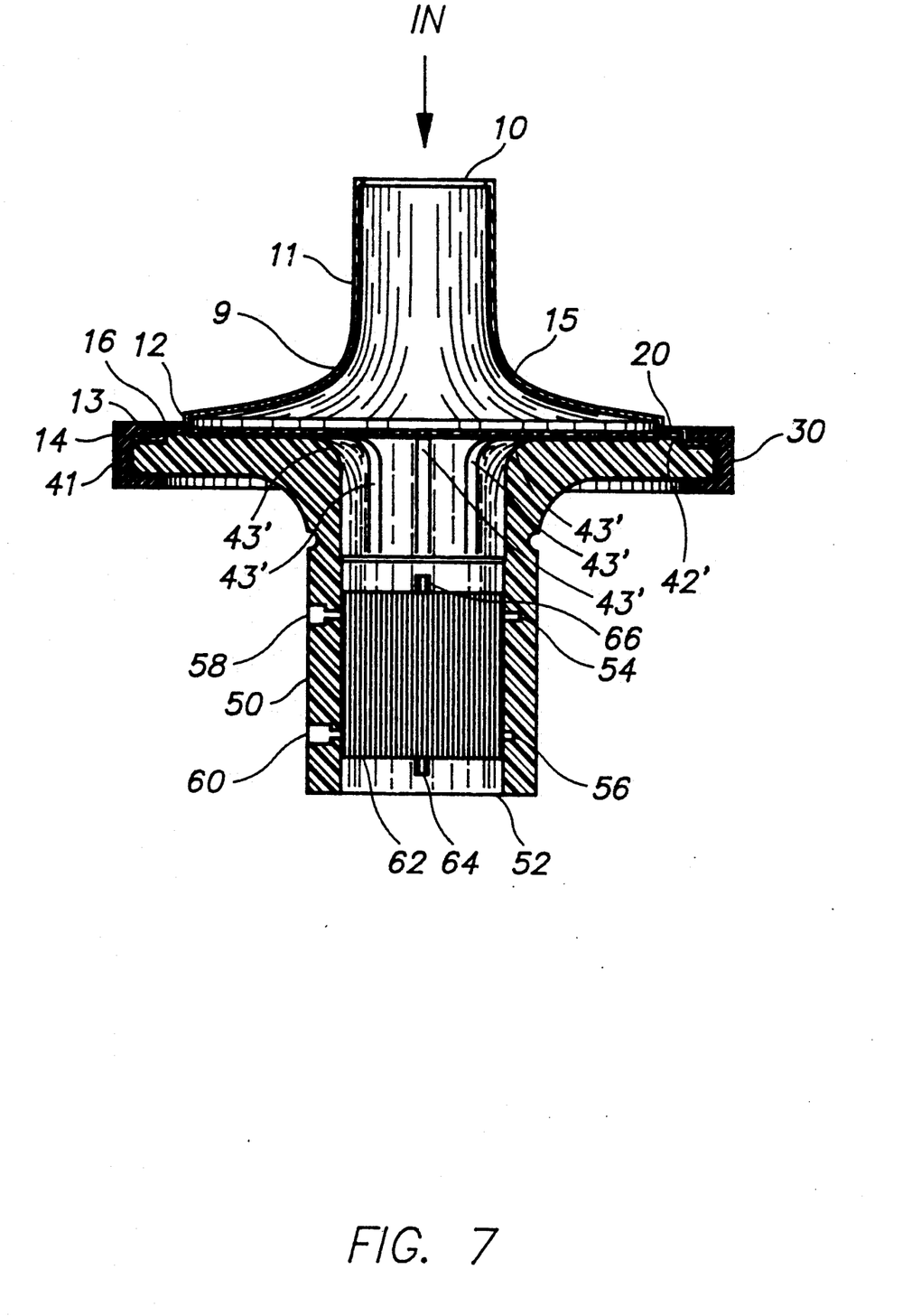
FIG. 7 is an assembled longitudinal cross-sectional view, taken along line 7—7 of FIG. 6.

Another air filter according to another embodiment of the present invention is shown in FIGS. 6 and 7 and is especially adapted for use with a pneumotachograph. A pneumotachograph measures the speed of air flow, but may also be used additionally to measure the volume of air displaced. Monitoring the speed of air flow helps indicate how the breathed air circulates, the magnitude of force exerted by the respiratory muscles during the different phases of respiration, and whether there is a pause at the end of the inspiration or the expiration.

The air filter shown in FIGS. 6 and 7, like the air filter shown in FIGS. 1-5, includes four separate components: a disposable shell 9 in all respects similar to the disposable shell 9 shown in FIGS. 1-5, a filter disk 20 in all respects similar to the filter disk 20 shown in FIGS. 1-5, a retaining band 30, in all respects similar to the retaining band 30 shown in FIGS. 1-5, and an equipment connection adaptor 50. The upper section of the equipment connection adaptor 50 is extremely similar to the upper section of the equipment connection adaptor 39. For example, the equipment connection adaptor 50 includes a coupling rim 41', a clamping ring 42', and a flaring tubular portion 46', in all respects similar to the corresponding numbered components of the equipment connection adaptor 39 shown in FIGS. 1-5. However, instead of the adaptor 50 possessing internal ribs 43, the adaptor 50 possesses a smooth, continuous L-shaped interior surface 43', as best shown in FIG. 7. The adaptor 50 also includes cylindrical outlet port 52.

The adaptor 50 may be formed of any of the materials of which the adaptor 39 may be fashioned.

As previously stated, the adaptor 50 is designed to be secured to a pneumotachograph. The pneumotachograph includes a cylindrically shaped plug 62 formed of corrugated metal. The outer peripheral surface of the plug 62 is provided with a series of spaced holes through which air entering the plug 62 may radially exit. A bobbin centrally, axially extends through the plug 62 to provide support and possesses an outer end 64 and an inner end 66.

As best shown in FIG. 7, the internal diameter of the adaptor 50 is approximately equal to the external diameter of the plug 62 so that the adaptor 50 may be mounted conformingly over the plug 62. The inner surface of the adaptor 50 includes an upper annular groove 54 and a lower annular groove 56 adapted to communicate with the exterior surface of the plug 62 when the adaptor 50 is mounted in the pneumotachograph. An upper port 58 and a lower port 60 extend radially through the wall of the adaptor 50 and communicate with the upper annular groove 54 and the lower annular groove 56, respectively.

Any change in the speed of breathing will cause a concomitant pressure differential to exist between the grooves 54, 56, and between the ports 58 and 60. This pressure differential may be measured and recorded in a well-known manner.

Like the air filter shown in FIGS. 1-5, the shell 9 and the filter disk 20 of the air filter shown in FIGS. 6 and 7 is adapted to be disposable and interchangeable, whereas, the retaining band 30 and the adaptor 50 are designed to be reusable.

Accordingly, as will be readily appreciated, the filter assembly of the present invention provides an inexpensive low flow resistance, partially disposable filter possessing a minimum of dead space which generates a minimum amount of medical waste, and which is readily adapted for use with a wide variety of medical ventilation and pulmonary testing equipment.

It is to be understood, however, that even though numerous characteristics and advantages of the present invention have been set forth in the foregoing description, together with details of the structure and function of the invention, the disclosure is illustrative only, and changes may be made in detail, especially in matters of materials, shape, size and arrangement of parts within the principles of the invention to the full extent indicated by the broad general meaning of the terms in which the appended claims ar expressed.

What is claimed is:

1. An air filter for medical ventilation equipment and the like, comprising:
   a shell possessing a substantially tubular conduit including an inlet aperture at a proximal end and terminating in an outwardly flaring surface, said conduit being substantially cylindrical and said outwardly flaring surface defined by the equation $R = A + BP^{(CD+G)}$ where R is the radius of the outwardly flaring surface from a central longitudinal axis of said conduit, A is the radius of the inlet aperture B is a selective variable, P is the base of the number system (e.g., 10 or e), C is a selective variable, D is the axial distance from a terminal end of said conduit at an intersection with said outwardly flaring surface, and G is a selective variable;
   an equipment connection adapter including an outlet aperture adapted for connection to conventional medical ventilation equipment;
   means for connecting said shell to said adapter in substantially fluid tight sealing relation; and
   filter media adapted for filtering fluids passing from said inlet aperture through said shell, said equipment connection adapter, and said outlet aperture.

2. The air filter of claim 1, wherein said filter media comprises an electret.

3. The air filter of claim 1, wherein said filter media comprises a substantially circular disk.

4. The air filter of claim 1, further comprising means securing said filter media to said shell.

5. The air filter of claim 4, wherein said means securing said filter media to said shell comprises an adhesive.

6. The air filter of claim 4, wherein said means for connecting said shell to said equipment connection adapter includes an elastic retaining band.

7. The air filter of claim 1, wherein said means for connecting said shell to said equipment connection adapter includes interfitting axially and radially sealing surfaces on said shell and said adapter.

8. The air filter of claim 1, further comprising an elastic retaining band possessing a circumferential groove engaging peripheral edge portions of said shell and said adapter.

9. The air filter of claim 8, further comprising at least one substantially circular sealing bead on an annular interior surface of said retaining band bounding said circumferential groove, said at least one sealing bead abutting at least one of said shell and said adapter.

10. The air filter of claim 1, wherein said adapter includes a plurality of circumferentially spaced ribs, said ribs each including a substantially radially extending portion for supporting said filter media.

11. The air filter of claim 1, further comprising:
   cooperating interfitting sealing surfaces on said shell and said adapter for connecting said shell to said adapter in substantially fluid tight sealing relation; and
   an elastic retaining band possessing a circumferential groove engaging peripheral edge portions of said shell and said adapter, said elastic retaining band releasably securing said shell and adapter in substantially fluid tight sealing relation such that said shell and said adapter may be readily disassembled and subsequently reassembled for reuse.

12. An air filter for medical ventilation equipment and the like, comprising:
   a disposable shell possessing a substantially tubular substantially cylindrical conduit including an inlet aperture at a proximal end and terminating in an exponentially outwardly flaring surface;
   said exponentially outwardly flaring surface defined by the equation $R = A + BP^{(CD+G)}$ where R is the radius of the outwardly flaring surface from a central longitudinal axis of said conduit, A is the radius of the inlet aperture, B is a selective variable, P is the base of the number system (e.g., 10 or e), C is a selective variable, D is the axial distance from a terminal end of said conduit at an intersection with said outwardly flaring surface, and G is a selective variable;
   an equipment connection adapter including an outlet aperture for connection to conventional medical ventilation equipment;
   a substantially circular filter disk secured within said disposable shell for filtering fluids passing from said inlet aperture through said disposable shell, said equipment connection adapter, and said outlet aperture;
   cooperating interfitting sealing surfaces on said disposable shell and said adapter for connecting said shell to said adapter in substantially fluid tight sealing relation; and
   an elastic retaining band possessing a circumferential groove engaging peripheral edge portions of said disposable shell and said adapter, said elastic retaining band releasably securing said disposable shell and said adapter in substantially fluid tight sealing relation such that said adapter may be readily disassembled from said disposable shell after use and subsequently reassembled to a new disposable shell tor reuse.

13. The air filter of claim 12, wherein said filter disk comprises an electret filter media.

14. The air filter of claim 12, further comprising an adhesive securing said filter media to said shell.

15. The air filter of claim 12, further comprising at least one substantially circular sealing bead on an annular interior surface of said retaining band bounding said circumferential groove, said at least one sealing bead abutting at least one of said shell and said adapter.

16. The air filter of claim 12, wherein said adapter includes a plurality of circumferentially spaced ribs, said ribs each including a substantially radially extending portion for supporting said filter disk.

17. An air filter for medical ventilation equipment and the like, comprising:
- a shell possessing a substantially tubular conduit including an inlet aperture at a proximal end and terminating in an outwardly flaring surface;
- an equipment connection adapter including an outlet aperture for connection to conventional medical ventilation equipment;
- a substantially circular filter disk secured within said shell for filtering fluids passing from said inlet aperture through said shell, said equipment connection adapter, and said outlet aperture;
- cooperating interfitting sealing surfaces on said disposable shell and said adapter for connecting said shell to said adapter in substantially fluid tight sealing relation, said cooperating interfitting sealing surfaces including:
- a first annular step on said shell disposed in a plane substantially perpendicular to a central longitudinal axis of said shell;
- said first annular step terminating in a substantially ninety degree junction with an axially extending cylindrical sidewall portion of said shell;
- said cylindrical sidewall portion terminating in a second annular step disposed in a plane substantially perpendicular to a central longitudinal axis of said shell;
- a coupling ring on said equipment adapter including a circular annular surface dimensioned for engagement with said second annular step;
- an upstanding circular clamping ring on said equipment adapter disposed radially inwardly of said circular annular surface of said coupling ring, said clamping ring dimensioned for clamping a circular outer peripheral edge portion of said filter disk against said first annular step; and
- means releasably securing said shell and said adapter in substantially fluid tight sealing relation such that said adapter may be readily disassembled from said shell after use and subsequently reassembled for reuse.

18. The air filter of claim 17, wherein said outwardly flaring surface comprises an exponentially outwardly flaring surface.

19. The air filter of claim 18, wherein said exponentially outwardly flaring surface is defined by the equation $R = A + BP^{(CD+G)}$ where R is the radius of the outwardly flaring surface from a central longitudinal axis of said conduit, A is the radius of the inlet aperture, B is a selective variable, P is the base of the number system (e.g., 10 or e), C is a selective variable, D is the axial distance from a terminal end of said conduit at an intersection with said outwardly flaring surface, and G is a selective variable.

20. The air filter of claim 17, wherein said filter disk comprises an electret filter media.

21. The air filter of claim 17, further comprising an adhesive securing said filter disk to said shell.

22. The air filter of claim 21, wherein said adhesive is disposed on said circular outer peripheral edge portion of said filter disk and secures said filter disk to said first annular step.

23. The air filter of claim 17, wherein said means for connecting said shell to said equipment connection adapter includes an elastic retaining band.

24. The air filter of claim 23, further comprising a circumferential groove in said elastic retaining band engaging peripheral edge portions of said shell and said adapter.

25. The air filter of claim 24, further comprising at least one substantially circular sealing bead on an annular interior surface of said retaining band bounding said circumferential groove, said at least one sealing bead abutting at least one of said shell and said adapter.

26. The air filter of claim 17, wherein said adapter includes a plurality of circumferentially spaced ribs, said ribs each including a substantially radially extending portion for supporting said filter disk.

* * * * *